US009714949B2

(12) United States Patent
Faatz et al.

(10) Patent No.: US 9,714,949 B2
(45) Date of Patent: Jul. 25, 2017

(54) ***VIBRIO CHOLERAE* LIPOPROTEIN 15 (LP15) VARIANTS AS ANTI-INTERFERENCE ADDITIVE IN TPN17-BASED IMMUNOASSAYS FOR DETECTION OF ANTI-*TREPONEMA* ANTIBODIES**

(71) Applicant: Roche Diagnostics Operations, Inc., Indianapolis, IN (US)

(72) Inventors: Elke Faatz, Huglfing (DE); Peter Schaarschmidt, Ulm (DE); Urban Schmitt, Kochel (DE); Christian Scholz, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/334,773

(22) Filed: Jul. 18, 2014

(65) Prior Publication Data

US 2015/0132859 A1 May 14, 2015

(30) Foreign Application Priority Data

Jul. 18, 2013 (EP) .................................... 13003633

(51) Int. Cl.

| | |
|---|---|
| ***G01N 33/53*** | (2006.01) |
| ***G01N 33/68*** | (2006.01) |
| ***C07K 14/28*** | (2006.01) |
| ***G01N 33/571*** | (2006.01) |
| ***C07K 14/245*** | (2006.01) |

(52) U.S. Cl.

CPC ....... *G01N 33/6854* (2013.01); *C07K 14/245* (2013.01); *C07K 14/28* (2013.01); *G01N 33/5306* (2013.01); *G01N 33/571* (2013.01); *C07K 2319/35* (2013.01); *G01N 2333/20* (2013.01); *G01N 2333/28* (2013.01); *G01N 2469/20* (2013.01); *G01N 2800/26* (2013.01)

(58) Field of Classification Search

None

See application file for complete search history.

(56) References Cited

FOREIGN PATENT DOCUMENTS

| | | | |
|---|---|---|---|
| DE | 102 07 135 | A1 | 9/2003 |
| EP | 2 127 678 | A1 | 12/2009 |
| WO | 03/000878 | A3 | 1/2003 |

OTHER PUBLICATIONS

George, R. et al., "An analysis of the value of some antigen-antibody interactions used as diagnostic indicators in a treponemal Western blot (TWB) test for syphilis," Journal of Clinical & Laboratory Immunology, 1998, pp. 27-44, vol. 50, No. 1, PMID:10189614 (PubMed-indexed for MEDLINE), Abstract, retrieved Jul. 18, 2014, 1 page.

Heidelberg, John F. et al., "DNA sequence of both chromosomes of the cholera pathogen Vibrio cholerae," Nature, 2000, pp. 477-484, vol. 406.

Pace, C. Nick et al., "How to measure and predict the molar absorption coefficient of a protein," Protein Science, 1995, pp. 2411-2423, vol. 4.

Rostopira, N. et al., "Elaboration of Enzyme Immunoassay Based on Recombinant Antigens and Intended for Diagnostics of Syphilis," Folia Microbiology, 2003, pp. 549-553, vol. 48, No. 4.

Scholz, Christian et al., "Functional Solubilization of Aggregation-prone HIV Envelope Proteins by Covalent Fusion with Chaperone Modules," Journal of Molecular Biology, 2005, pp. 1229-1241, vol. 345.

*Primary Examiner* — Ja'na Hines

*Assistant Examiner* — Khatol Shahnan Shah

(74) *Attorney, Agent, or Firm* — Roche Diagnostics Operations, Inc.

(57) ABSTRACT

The invention relates to a method for detecting antibodies against the TpN17 antigen of *Treponema pallidum* in an isolated sample wherein a peptide sequence of *Vibrio cholerae* lipoprotein 15 (VcLp15) or a partial sequence thereof is used as a reagent for reduction of interference, i.e. for minimizing false positive results. In addition the invention relates to fusion polypeptides comprising a VcLp15 peptide sequence and a chaperone, to their use as an additive in an immunoassay for said reduction of interferences and for minimizing false positive results and to a reagent kit for detecting antibodies against *Treponema pallidum* antigens in an isolated sample comprising a TpN17 antigen and said VcLp15-chaperone fusion polypeptide.

7 Claims, 2 Drawing Sheets

SEQUENCE LISTING

```
<160> NUMBER OF SEQ ID NOS: 12

<210> SEQ ID NO 1
<211> LENGTH: 163
<212> TYPE: PRT
<213> ORGANISM: Vibrio cholerae

<400> SEQUENCE: 1

Met Met Lys Lys Ser Ile Phe Ala Leu Ser Ala Leu Thr Leu Ile Leu
1               5                   10                  15

Val Gly Cys Asp Asn Gln Gln Asp Ala Lys Val Glu Val Glu Lys Val
            20                  25                  30

Val Asp Val Ala Ala Ala Pro Ala Glu Gln Ser Ala Ala Gln Pro Ser
        35                  40                  45

Thr Ala Ser Val Asp Ala Ala His Asn Ala Gln Asn Ser Leu Asp Trp
    50                  55                  60

Ala Gly Ile Tyr Gln Gly Thr Leu Pro Cys Ala Asp Cys Gly Gly Ile
65                  70                  75                  80

Glu Thr Glu Leu Thr Leu Asn Ala Asp Gly Thr Tyr Ala Leu Thr Glu
                85                  90                  95

Lys Tyr Leu Asp Lys Glu Gly Glu Pro Phe Ala Ser Gln Gly Thr Phe
            100                 105                 110

Val Trp Asn Glu Ala Gly Asn Ile Val Thr Leu Gln Thr Gly Asp Gln
        115                 120                 125

Thr Gly Arg Gln Phe Met Val Gly Glu Asn Thr Leu Ser His Leu Asp
    130                 135                 140

Met Glu Gly Lys Val Ile Glu Gly Glu Leu Ala Glu Phe Tyr Val Leu
145                 150                 155                 160

Ser Lys Gln
```

-continued

<210> SEQ ID NO 2
<211> LENGTH: 146
<212> TYPE: PRT
<213> ORGANISM: Artificial Sequence
<220> FEATURE:
<223> OTHER INFORMATION: VcLp15 with hexa-his tag at c-terminal end

<400> SEQUENCE: 2

```
Lys Val Glu Val Glu Lys Val Val Asp Val Ala Ala Ala Pro Ala Glu
1               5                   10                  15

Gln Ser Ala Ala Gln Pro Ser Thr Ala Ser Val Asp Ala Ala His Asn
            20                  25                  30

Ala Gln Asn Ser Leu Asp Trp Ala Gly Ile Tyr Gln Gly Thr Leu Pro
        35                  40                  45

Ala Ala Asp Ala Gly Gly Ile Glu Thr Glu Leu Thr Leu Asn Ala Asp
    50                  55                  60

Gly Thr Tyr Ala Leu Thr Glu Lys Tyr Leu Asp Lys Glu Gly Glu Pro
65                  70                  75                  80

Phe Ala Ser Gln Gly Thr Phe Val Trp Asn Glu Ala Gly Asn Ile Val
                85                  90                  95

Thr Leu Gln Thr Gly Asp Gln Thr Gly Arg Gln Phe Met Val Gly Glu
            100                 105                 110

Asn Thr Leu Ser His Leu Asp Met Glu Gly Lys Val Ile Glu Gly Glu
        115                 120                 125

Leu Ala Glu Phe Tyr Val Leu Ser Lys Gln Leu Glu His His His His
    130                 135                 140

His His
145
```

<210> SEQ ID NO 3
<211> LENGTH: 334
<212> TYPE: PRT
<213> ORGANISM: artificial
<220> FEATURE:
<223> OTHER INFORMATION: EcSlyD-VcLp15

<400> SEQUENCE: 3

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160
```

-continued

```
Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Glu Val
            180                 185                 190

Glu Lys Val Val Asp Val Ala Ala Ala Pro Ala Glu Gln Ser Ala Ala
        195                 200                 205

Gln Pro Ser Thr Ala Ser Val Asp Ala Ala His Asn Ala Gln Asn Ser
    210                 215                 220

Leu Asp Trp Ala Gly Ile Tyr Gln Gly Thr Leu Pro Ala Ala Asp Ala
225                 230                 235                 240

Gly Gly Ile Glu Thr Glu Leu Thr Leu Asn Ala Asp Gly Thr Tyr Ala
                245                 250                 255

Leu Thr Glu Lys Tyr Leu Asp Lys Glu Gly Glu Pro Phe Ala Ser Gln
            260                 265                 270

Gly Thr Phe Val Trp Asn Glu Ala Gly Asn Ile Val Thr Leu Gln Thr
        275                 280                 285

Gly Asp Gln Thr Gly Arg Gln Phe Met Val Gly Glu Asn Thr Leu Ser
    290                 295                 300

His Leu Asp Met Glu Gly Lys Val Ile Glu Gly Glu Leu Ala Glu Phe
305                 310                 315                 320

Tyr Val Leu Ser Lys Gln Leu Glu His His His His His His
                325                 330


<210> SEQ ID NO 4
<211> LENGTH: 311
<212> TYPE: PRT
<213> ORGANISM: Artificial
<220> FEATURE:
<223> OTHER INFORMATION: EcSkp-VcLp15

<400> SEQUENCE: 4

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
    50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Arg Ser Asn Glu Glu Arg Gly Lys
                85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
        115                 120                 125

Asp Val Lys Asp Ile Thr Ala Asp Val Leu Lys Gln Val Lys Gly Gly
    130                 135                 140

Gly Ser Gly Gly Gly Ser Gly Gly Gly Ser Gly Gly Gly Ser Gly Gly
145                 150                 155                 160

Gly Ser Gly Gly Gly Lys Val Glu Val Glu Lys Val Val Asp Val Ala
                165                 170                 175

Ala Ala Pro Ala Glu Gln Ser Ala Ala Gln Pro Ser Thr Ala Ser Val
            180                 185                 190
```

```
Asp Ala Ala His Asn Ala Gln Asn Ser Leu Asp Trp Ala Gly Ile Tyr
        195                 200                 205

Gln Gly Thr Leu Pro Ala Ala Asp Ala Gly Gly Ile Glu Thr Glu Leu
    210                 215                 220

Thr Leu Asn Ala Asp Gly Thr Tyr Ala Leu Thr Glu Lys Tyr Leu Asp
225                 230                 235                 240

Lys Glu Gly Glu Pro Phe Ala Ser Gln Gly Thr Phe Val Trp Asn Glu
                245                 250                 255

Ala Gly Asn Ile Val Thr Leu Gln Thr Gly Asp Gln Thr Gly Arg Gln
            260                 265                 270

Phe Met Val Gly Glu Asn Thr Leu Ser His Leu Asp Met Glu Gly Lys
        275                 280                 285

Val Ile Glu Gly Glu Leu Ala Glu Phe Tyr Val Leu Ser Lys Gln Leu
    290                 295                 300

Glu His His His His His His
305                 310


<210> SEQ ID NO 5
<211> LENGTH: 156
<212> TYPE: PRT
<213> ORGANISM: Treponema pallidum

<400> SEQUENCE: 5

Met Lys Gly Ser Val Arg Ala Leu Cys Ala Phe Leu Gly Val Gly Ala
1               5                   10                  15

Leu Gly Ser Ala Leu Cys Val Ser Cys Thr Thr Val Cys Pro His Ala
            20                  25                  30

Gly Lys Ala Lys Ala Glu Lys Val Glu Cys Ala Leu Lys Gly Gly Ile
        35                  40                  45

Phe Arg Gly Thr Leu Pro Ala Ala Asp Cys Pro Gly Ile Asp Thr Thr
    50                  55                  60

Val Thr Phe Asn Ala Asp Gly Thr Ala Gln Lys Val Glu Leu Ala Leu
65                  70                  75                  80

Glu Lys Lys Ser Ala Pro Ser Pro Leu Thr Tyr Arg Gly Thr Trp Met
                85                  90                  95

Val Arg Glu Asp Gly Ile Val Glu Leu Ser Leu Val Ser Ser Glu Gln
            100                 105                 110

Ser Lys Ala Pro His Glu Lys Glu Leu Tyr Glu Leu Ile Asp Ser Asn
        115                 120                 125

Ser Val Arg Tyr Met Gly Ala Pro Gly Ala Gly Lys Pro Ser Lys Glu
    130                 135                 140

Met Ala Pro Phe Tyr Val Leu Lys Lys Thr Lys Lys
145                 150                 155


<210> SEQ ID NO 6
<211> LENGTH: 134
<212> TYPE: PRT
<213> ORGANISM: Artificial
<220> FEATURE:
<223> OTHER INFORMATION: TpN17 23-156 with Cys to Ala mutations

<400> SEQUENCE: 6

Val Ser Ala Thr Thr Val Ala Pro His Ala Gly Lys Ala Lys Ala Glu
1               5                   10                  15

Lys Val Glu Ala Ala Leu Lys Gly Gly Ile Phe Arg Gly Thr Leu Pro
            20                  25                  30
```

-continued

Ala Ala Asp Ala Pro Gly Ile Asp Thr Thr Val Thr Phe Asn Ala Asp
        35                  40                  45

Gly Thr Ala Gln Lys Val Glu Leu Ala Leu Glu Lys Lys Ser Ala Pro
    50                  55                  60

Ser Pro Leu Thr Tyr Arg Gly Thr Trp Met Val Arg Glu Asp Gly Ile
65                  70                  75                  80

Val Glu Leu Ser Leu Val Ser Ser Glu Gln Ser Lys Ala Pro His Glu
                85                  90                  95

Lys Glu Leu Tyr Glu Leu Ile Asp Ser Asn Ser Val Arg Tyr Met Gly
            100                 105                 110

Ala Pro Gly Ala Gly Lys Pro Ser Lys Glu Met Ala Pro Phe Tyr Val
        115                 120                 125

Leu Lys Lys Thr Lys Lys
    130

<210> SEQ ID NO 7
<211> LENGTH: 142
<212> TYPE: PRT
<213> ORGANISM: Artificial
<220> FEATURE:
<223> OTHER INFORMATION: TpN17 with hexa-his

<400> SEQUENCE: 7

Val Ser Ala Thr Thr Val Ala Pro His Ala Gly Lys Ala Lys Ala Glu
1               5                   10                  15

Lys Val Glu Ala Ala Leu Lys Gly Gly Ile Phe Arg Gly Thr Leu Pro
            20                  25                  30

Ala Ala Asp Ala Pro Gly Ile Asp Thr Thr Val Thr Phe Asn Ala Asp
        35                  40                  45

Gly Thr Ala Gln Lys Val Glu Leu Ala Leu Glu Lys Lys Ser Ala Pro
    50                  55                  60

Ser Pro Leu Thr Tyr Arg Gly Thr Trp Met Val Arg Glu Asp Gly Ile
65                  70                  75                  80

Val Glu Leu Ser Leu Val Ser Ser Glu Gln Ser Lys Ala Pro His Glu
                85                  90                  95

Lys Glu Leu Tyr Glu Leu Ile Asp Ser Asn Ser Val Arg Tyr Met Gly
            100                 105                 110

Ala Pro Gly Ala Gly Lys Pro Ser Lys Glu Met Ala Pro Phe Tyr Val
        115                 120                 125

Leu Lys Lys Thr Lys Lys Leu Glu His His His His His His
    130                 135                 140

<210> SEQ ID NO 8
<211> LENGTH: 517
<212> TYPE: PRT
<213> ORGANISM: Artificial
<220> FEATURE:
<223> OTHER INFORMATION: E.coli tandem-SlyD fused to TpN17

<400> SEQUENCE: 8

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

```
Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Val Ser Ala Thr Thr Val Ala Pro His
    370                 375                 380

Ala Gly Lys Ala Lys Ala Glu Lys Val Glu Ala Ala Leu Lys Gly Gly
385                 390                 395                 400

Ile Phe Arg Gly Thr Leu Pro Ala Ala Asp Ala Pro Gly Ile Asp Thr
                405                 410                 415

Thr Val Thr Phe Asn Ala Asp Gly Thr Ala Gln Lys Val Glu Leu Ala
            420                 425                 430

Leu Glu Lys Lys Ser Ala Pro Ser Pro Leu Thr Tyr Arg Gly Thr Trp
        435                 440                 445

Met Val Arg Glu Asp Gly Ile Val Glu Leu Ser Leu Val Ser Ser Glu
    450                 455                 460

Gln Ser Lys Ala Pro His Glu Lys Glu Leu Tyr Glu Leu Ile Asp Ser
465                 470                 475                 480
```

-continued

```
Asn Ser Val Arg Tyr Met Gly Ala Pro Gly Ala Gly Lys Pro Ser Lys
                485                 490                 495

Glu Met Ala Pro Phe Tyr Val Leu Lys Lys Thr Lys Lys Leu Glu His
            500                 505                 510

His His His His His
        515


<210> SEQ ID NO 9
<211> LENGTH: 497
<212> TYPE: PRT
<213> ORGANISM: Artificial
<220> FEATURE:
<223> OTHER INFORMATION: Pasteurella multocida tandem-SlyDTpN17

<400> SEQUENCE: 9

Met Lys Ile Ala Lys Asn Val Val Val Ser Ile Ala Tyr Gln Val Arg
1               5                   10                  15

Thr Glu Asp Gly Val Leu Val Asp Glu Ala Pro Val Asn Gln Pro Leu
            20                  25                  30

Glu Tyr Leu Gln Gly His Asn Asn Leu Val Ile Gly Leu Glu Asn Ala
        35                  40                  45

Leu Glu Gly Lys Ala Val Gly Asp Lys Phe Glu Val Arg Val Lys Pro
    50                  55                  60

Glu Glu Ala Tyr Gly Glu Tyr Asn Glu Asn Met Val Gln Arg Val Pro
65                  70                  75                  80

Lys Asp Val Phe Gln Gly Val Asp Glu Leu Val Val Gly Met Arg Phe
                85                  90                  95

Ile Ala Asp Thr Asp Ile Gly Pro Leu Pro Val Val Ile Thr Glu Val
            100                 105                 110

Ala Glu Asn Asp Val Val Val Asp Gly Asn His Met Leu Ala Gly Gln
        115                 120                 125

Glu Leu Leu Phe Ser Val Glu Val Val Ala Thr Arg Glu Ala Thr Leu
    130                 135                 140

Glu Glu Ile Ala His Gly His Ile His Gln Glu Gly Gly Gly Gly Ser
145                 150                 155                 160

Gly Gly Gly Ser Gly Gly Gly Gly Gly Ser Gly Gly Gly Ser Gly Gly
                165                 170                 175

Gly Lys Ile Ala Lys Asn Val Val Val Ser Ile Ala Tyr Gln Val Arg
            180                 185                 190

Thr Glu Asp Gly Val Leu Val Asp Glu Ala Pro Val Asn Gln Pro Leu
        195                 200                 205

Glu Tyr Leu Gln Gly His Asn Asn Leu Val Ile Gly Leu Glu Asn Ala
    210                 215                 220

Leu Glu Gly Lys Ala Val Gly Asp Lys Phe Glu Val Arg Val Lys Pro
225                 230                 235                 240

Glu Glu Ala Tyr Gly Glu Tyr Asn Glu Asn Met Val Gln Arg Val Pro
                245                 250                 255

Lys Asp Val Phe Gln Gly Val Asp Glu Leu Val Val Gly Met Arg Phe
            260                 265                 270

Ile Ala Asp Thr Asp Ile Gly Pro Leu Pro Val Val Ile Thr Glu Val
        275                 280                 285

Ala Glu Asn Asp Val Val Val Asp Gly Asn His Met Leu Ala Gly Gln
    290                 295                 300

Glu Leu Leu Phe Ser Val Glu Val Val Ala Thr Arg Glu Ala Thr Leu
305                 310                 315                 320
```

-continued

```
Glu Glu Ile Ala His Gly His Ile His Gln Glu Gly Gly Gly Gly Ser
                325                 330                 335

Gly Gly Gly Ser Gly Gly Gly Ser Gly Gly Gly Ser Gly Gly Gly Ser
            340                 345                 350

Gly Gly Gly Val Ser Ala Thr Thr Val Ala Pro His Ala Gly Lys Ala
        355                 360                 365

Lys Ala Glu Lys Val Glu Ala Ala Leu Lys Gly Gly Ile Phe Arg Gly
    370                 375                 380

Thr Leu Pro Ala Ala Asp Ala Pro Gly Ile Asp Thr Thr Val Thr Phe
385                 390                 395                 400

Asn Ala Asp Gly Thr Ala Gln Lys Val Glu Leu Ala Leu Glu Lys Lys
                405                 410                 415

Ser Ala Pro Ser Pro Leu Thr Tyr Arg Gly Thr Trp Met Val Arg Glu
            420                 425                 430

Asp Gly Ile Val Glu Leu Ser Leu Val Ser Ser Glu Gln Ser Lys Ala
        435                 440                 445

Pro His Glu Lys Glu Leu Tyr Glu Leu Ile Asp Ser Asn Ser Val Arg
    450                 455                 460

Tyr Met Gly Ala Pro Gly Ala Gly Lys Pro Ser Lys Glu Met Ala Pro
465                 470                 475                 480

Phe Tyr Val Leu Lys Lys Thr Lys Lys Leu Glu His His His His His
                485                 490                 495

His


<210> SEQ ID NO 10
<211> LENGTH: 411
<212> TYPE: PRT
<213> ORGANISM: Artificial
<220> FEATURE:
<223> OTHER INFORMATION: E. coli FkpA-TpN17

<400> SEQUENCE: 10

Met Ala Glu Ala Ala Lys Pro Ala Thr Thr Ala Asp Ser Lys Ala Ala
1               5                   10                  15

Phe Lys Asn Asp Asp Gln Lys Ser Ala Tyr Ala Leu Gly Ala Ser Leu
            20                  25                  30

Gly Arg Tyr Met Glu Asn Ser Leu Lys Glu Gln Glu Lys Leu Gly Ile
        35                  40                  45

Lys Leu Asp Lys Asp Gln Leu Ile Ala Gly Val Gln Asp Ala Phe Ala
    50                  55                  60

Asp Lys Ser Lys Leu Ser Asp Gln Glu Ile Glu Gln Thr Leu Gln Ala
65                  70                  75                  80

Phe Glu Ala Arg Val Lys Ser Ser Ala Gln Ala Lys Met Glu Lys Asp
                85                  90                  95

Ala Ala Asp Asn Glu Ala Lys Gly Lys Glu Tyr Arg Glu Lys Phe Ala
            100                 105                 110

Lys Glu Lys Gly Val Lys Thr Ser Ser Thr Gly Leu Val Tyr Gln Val
        115                 120                 125

Val Glu Ala Gly Lys Gly Glu Ala Pro Lys Asp Ser Asp Thr Val Val
    130                 135                 140

Val Asn Tyr Lys Gly Thr Leu Ile Asp Gly Lys Glu Phe Asp Asn Ser
145                 150                 155                 160

Tyr Thr Arg Gly Glu Pro Leu Ser Phe Arg Leu Asp Gly Val Ile Pro
                165                 170                 175

Gly Trp Thr Glu Gly Leu Lys Asn Ile Lys Lys Gly Gly Lys Ile Lys
```

```
            180                 185                 190

Leu Val Ile Pro Pro Glu Leu Ala Tyr Gly Lys Ala Gly Val Pro Gly
        195                 200                 205

Ile Pro Pro Asn Ser Thr Leu Val Phe Asp Val Glu Leu Leu Asp Val
    210                 215                 220

Lys Pro Ala Pro Lys Ala Asp Ala Lys Pro Glu Ala Asp Ala Lys Ala
225                 230                 235                 240

Ala Asp Ser Ala Lys Lys Gly Gly Gly Ser Gly Gly Gly Ser Gly Gly
                245                 250                 255

Gly Ser Gly Gly Gly Ser Gly Gly Gly Ser Gly Gly Gly Val Ser Ala
            260                 265                 270

Thr Thr Val Ala Pro His Ala Gly Lys Ala Lys Ala Glu Lys Val Glu
        275                 280                 285

Ala Ala Leu Lys Gly Gly Ile Phe Arg Gly Thr Leu Pro Ala Ala Asp
    290                 295                 300

Ala Pro Gly Ile Asp Thr Thr Val Thr Phe Asn Ala Asp Gly Thr Ala
305                 310                 315                 320

Gln Lys Val Glu Leu Ala Leu Glu Lys Lys Ser Ala Pro Ser Pro Leu
                325                 330                 335

Thr Tyr Arg Gly Thr Trp Met Val Arg Glu Asp Gly Ile Val Glu Leu
            340                 345                 350

Ser Leu Val Ser Ser Glu Gln Ser Lys Ala Pro His Glu Lys Glu Leu
        355                 360                 365

Tyr Glu Leu Ile Asp Ser Asn Ser Val Arg Tyr Met Gly Ala Pro Gly
    370                 375                 380

Ala Gly Lys Pro Ser Lys Glu Met Ala Pro Phe Tyr Val Leu Lys Lys
385                 390                 395                 400

Thr Lys Lys Leu Glu His His His His His His
                405                 410


<210> SEQ ID NO 11
<211> LENGTH: 307
<212> TYPE: PRT
<213> ORGANISM: Artificial
<220> FEATURE:
<223> OTHER INFORMATION: E. coli Skp-TpN17

<400> SEQUENCE: 11

Met Ala Asp Lys Ile Ala Ile Val Asn Met Gly Ser Leu Phe Gln Gln
1               5                   10                  15

Val Ala Gln Lys Thr Gly Val Ser Asn Thr Leu Glu Asn Glu Phe Arg
            20                  25                  30

Gly Arg Ala Ser Glu Leu Gln Arg Met Glu Thr Asp Leu Gln Ala Lys
        35                  40                  45

Met Lys Lys Leu Gln Ser Met Lys Ala Gly Ser Asp Arg Thr Lys Leu
    50                  55                  60

Glu Lys Asp Val Met Ala Gln Arg Gln Thr Phe Ala Gln Lys Ala Gln
65                  70                  75                  80

Ala Phe Glu Gln Asp Arg Ala Arg Arg Ser Asn Glu Glu Arg Gly Lys
                85                  90                  95

Leu Val Thr Arg Ile Gln Thr Ala Val Lys Ser Val Ala Asn Ser Gln
            100                 105                 110

Asp Ile Asp Leu Val Val Asp Ala Asn Ala Val Ala Tyr Asn Ser Ser
        115                 120                 125

Asp Val Lys Asp Ile Thr Ala Asp Val Leu Lys Gln Val Lys Gly Gly
```

-continued

```
    130                 135                 140

Gly Ser Gly Gly Gly Ser Gly Gly Gly Ser Gly Gly Gly Ser Gly Gly
145                 150                 155                 160

Gly Ser Gly Gly Gly Val Ser Ala Thr Thr Val Ala Pro His Ala Gly
                165                 170                 175

Lys Ala Lys Ala Glu Lys Val Glu Ala Ala Leu Lys Gly Gly Ile Phe
            180                 185                 190

Arg Gly Thr Leu Pro Ala Ala Asp Ala Pro Gly Ile Asp Thr Thr Val
        195                 200                 205

Thr Phe Asn Ala Asp Gly Thr Ala Gln Lys Val Glu Leu Ala Leu Glu
    210                 215                 220

Lys Lys Ser Ala Pro Ser Pro Leu Thr Tyr Arg Gly Thr Trp Met Val
225                 230                 235                 240

Arg Glu Asp Gly Ile Val Glu Leu Ser Leu Val Ser Ser Glu Gln Ser
                245                 250                 255

Lys Ala Pro His Glu Lys Glu Leu Tyr Glu Leu Ile Asp Ser Asn Ser
            260                 265                 270

Val Arg Tyr Met Gly Ala Pro Gly Ala Gly Lys Pro Ser Lys Glu Met
        275                 280                 285

Ala Pro Phe Tyr Val Leu Lys Lys Thr Lys Lys Leu Glu His His His
    290                 295                 300

His His His
305


<210> SEQ ID NO 12
<211> LENGTH: 23
<212> TYPE: PRT
<213> ORGANISM: Artificial
<220> FEATURE:
<223> OTHER INFORMATION: Glycine rich linker

<400> SEQUENCE: 12

Gly Gly Gly Ser Gly Gly Gly Ser Gly Gly Gly Ser Gly Gly Gly Ser
1               5                   10                  15

Gly Gly Gly Ser Gly Gly Gly
            20
```

*VIBRIO CHOLERAE* LIPOPROTEIN 15 (LP15) VARIANTS AS ANTI-INTERFERENCE ADDITIVE IN TPN17-BASED IMMUNOASSAYS FOR DETECTION OF ANTI-*TREPONEMA* ANTIBODIES

RELATED APPLICATIONS

This application claims the benefit of European Patent Application No. 13003633.8 filed Jul. 18, 2013, the disclosure of which is hereby incorporated by reference in its entirety.

FIELD OF THE INVENTION

The invention relates to a method for detecting antibodies against the TpN17 antigen of *Treponema pallidum* in an isolated sample wherein a peptide sequence of *Vibrio cholerae* lipoprotein 15 (VcLp15) is used as a reagent for reduction of interference and for minimizing false positive results. In addition the invention relates to fusion polypeptides comprising a VcLp15 peptide sequence and a chaperone, to their use as an additive in an immunoassay for reduction of interferences and for minimizing false positive results and to a reagent kit for detecting antibodies against *Treponema pallidum* antigens in an isolated sample comprising a TpN17 antigen and said VcLp15-chaperone fusion polypeptide.

BACKGROUND OF THE INVENTION

Syphilis, also called Lues, is a severe infectious disease which is caused by *Treponema pallidum*, belonging to the bacterial family of spirochetes. It is mainly transmitted by sexual contact but can also be passed from an expectant mother to the unborn during pregnancy. The disease is characterized by distinct clinical stages and long periods of latent, asymptomatic infection. Many infected individuals do not notice symptoms and thus are unaware of their syphilis infection for years. The primary infection is confined and usually causes a small painless ulcer (primary stage, "Lues I"). If left untreated by penicillin, the disease proceeds to the secondary stage Lues II (about eight weeks after infection), which entails flu-like symptoms, non-itchy skin rash and swollen lymph nodes. After some years, at stage Lues III, syphilitic nodes appear throughout the body. The final stage (Lues IV) is characterized by destruction of the central nervous system eventually leading to neurological and cardiological disorders, general paralysis, ataxia, dementia and blindness.

Although effective therapies have been available since the introduction of penicillin in the mid-20th century, syphilis still remains an important global health problem with estimated 12 million new infections worldwide each year. It is necessary to reliably identify patients with *Treponema* infection in order to initiate antibiotic therapy and thus to prevent the further spread of syphilis. As a consequence, it is necessary to provide reliable diagnostic tools such as immunoassays for the detection of antibodies against *Treponema pallidum*. Yet, in order to be used as specific compounds in serological applications, recombinant-derived proteins have to meet several requirements such as solubility, stability and antigenicity.

TpN17 (*Treponema pallidum* strain Nichols, 17 kDa), a small protein that consists of 134 amino acid residues in its mature form, is the immunodominant antigen of *Treponema pallidum*, the causative agent of Syphilis (J. Clin. Lab.

Immunol. (1998), 50, 27-44; Folia Microbial. (2003) 48 (4), 549-553). Antibodies towards TpN17 are frequent and abundant in *Treponema*-infected individuals, and thus it is advantageous to use TpN17 in certain embodiments of an immunoassay that aims at the sensitive and reliable detection of *Treponema* infections.

However, we observed that an immunoassay using TpN17 as an antigen tends to show false positive results, i.e. it provides a seemingly positive signal although in fact no antibodies against *Treponema* are present in that sample. These interferences are a rare but significant phenomenon. They compromise the specificity of the immunoassay and they are clearly due to the use of the *Treponema pallidum* antigen TpN17, which is virtually indispensable in a Syphilis immunoassay.

The problem underlying the current invention can therefore be seen in providing means and methods for avoiding false positive results and increasing the specificity of TpN17-based immunoassays for the detection of anti-*Treponema* antibodies.

SUMMARY OF THE INVENTION

The problem is solved by the current invention as characterized by the claims. In particular, the invention concerns a method for detecting antibodies against the TpN17 antigen of *Treponema pallidum* in an isolated sample wherein a peptide sequence of *Vibrio cholerae* lipoprotein 15 (VcLp15) or a partial sequence thereof is used as a reagent for reduction of interference, i.e. for minimizing false positive results. Said partial sequence of the VcLp15 polypeptide sequence can comprise amino acids 26-163 of SEQ ID NO. 1. In a further embodiment said VcLp15 peptide sequence or partial sequence thereof is fused to a chaperone.

The invention also relates to a fusion polypeptide comprising a VcLp15 peptide sequence according to SEQ ID NO. 1 or a partial sequence thereof and a chaperone. In certain embodiments the chaperone fused to the VcLp15 peptide sequence is selected from the group consisting of SlyD, SlpA, FkpA, and Skp.

In another embodiment the fusion polypeptide comprises SEQ ID NO. 3 which is a fusion polypeptide of *E. coli* SlyD and VcLp15 (EcSlyD-VcLp15).

Also encompassed by the current invention is the use of a fusion polypeptide comprising a VcLp15 peptide and optionally a chaperone as an additive in an immunoassay for reduction of interferences and for minimizing false positive results.

In a further embodiment the invention concerns a reagent kit for the detection of antibodies against *Treponema pallidum* antigens in an isolated sample by an immunoassay, comprising a TpN17 antigen and a fusion polypeptide comprising a VcLp15 peptide and optionally a chaperone.

The current invention also relates to a method for detecting antibodies against the TpN17 antigen of *Treponema pallidum* in an isolated sample, said method comprising a) forming an immunoreaction admixture by admixing a body fluid sample with a specific binding partner that can be specifically bound by said antibodies present in said sample b) adding a fusion polypeptide comprising a VcLp15 peptide and optionally a chaperone to said immunoreaction admixture either before, at the same time or after said specific binding partner is added to said sample c) maintaining said immunoreaction admixture for a time period sufficient for allowing the antibodies present in said body fluid sample to immunoreact with said specific binding partner to form an immunoreaction product; and d) detecting the presence and/or the concentration of any of said immunoreaction product.

BRIEF DESCRIPTION OF THE FIGURES, TABLES AND SEQ ID NOS.

Figure 1:
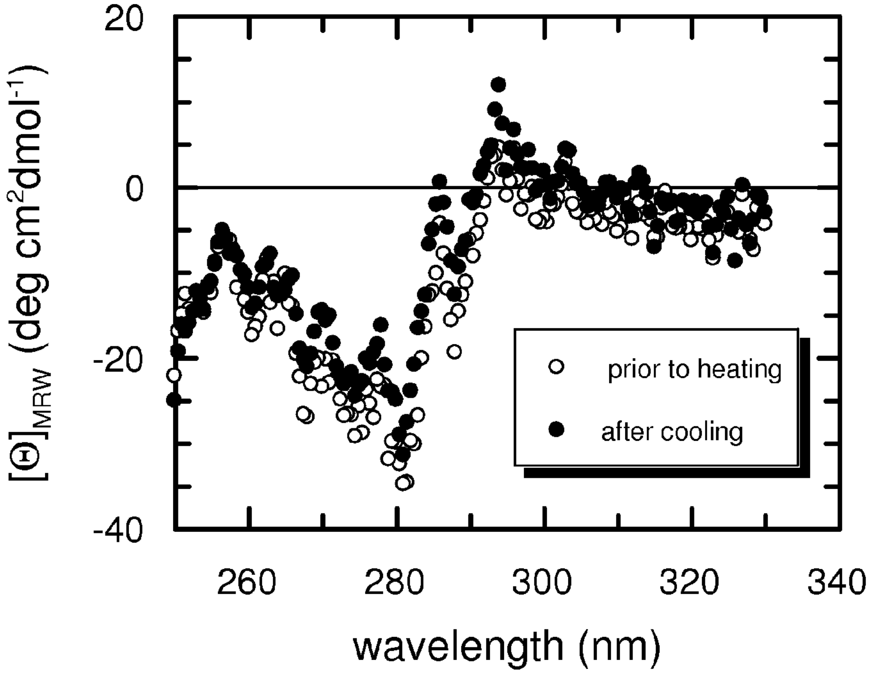
FIG. 1 shows near UV CD spectra (ultra-violet circular dichroism spectra) of the fusion polypeptide EcSlyD-VcLp15 according to the invention; for more details refer to example 4 describing the thermally induced unfolding of EcSlyD-VcLp15 as monitored by CD spectroscopy.

Table 1 shows protein parameters of the fusion polypeptide variants used in this study (example 2)

Tables 2 to 5 show the results of the experiments performed according to example 5 on the anti-interference activity of *Vibrio cholerae* Lp15 in a syphilis immunoassay.

Table 2 shows the results for oligomeric TpN17 as *Treponema*-specific antigen wherein monomeric VcLp15 (fused with SlyD as a chaperone) is added for interference reduction.

Table 3 shows the results for monomeric TpN17 as *Treponema*-specific antigen wherein monomeric VcLp15 (fused with SlyD as a chaperone) is added for interference reduction.

Table 4 shows the results for oligomeric TpN17 as *Treponema*-specific antigen wherein oligomeric VcLp15 (fused with Skp as a chaperone) is added for interference reduction.

Table 5 shows the results for monomeric TpN17 as *Treponema*-specific antigen wherein oligomeric VcLp15 (fused with Skp as a chaperone) is added for interference reduction.

SEQ ID NO. 1 shows the complete amino acid sequence (163 residues) of *Vibrio cholerae* lipoprotein 15 (VcLp15) as retrievable from the public database UniProt, accession no. Q9KQN6. Amino acid residues 1-25 constitute the signal sequence; the mature VcLp15 comprises amino acid residues 26-163 (underlined).

```
MMKKSIFALS ALTLILVGCD NQQDAKVEVE KVVDVAAAPA
EQSAAQPSTA SVDAAHNAQN SLDWAGIYQG TLPCADCGGI
ETELTLNADG TYALTEKYLD KEGEPFASQG TFVWNEAGNI
VTLQTGDQTG RQFMVGENTL SHLDMEGKVI EGELAEFYVL SKQ
```

SEQ ID NO. 2 shows the VcLp15 sequence (26-163) as used in fusion with different chaperone modules. The mature VcLp15 sequence (amino acid residues 26-163) is lacking the N-terminal signal sequence (amino acid residues 1-25) and is devoid of cysteine residues. The two genuine cysteine residues of VcLp15 at the positions 74 and 77 [numbering of precursor protein] were replaced by alanine residues—underlined—in order to facilitate the refolding process and to suppress disulfide adduct formation. VcLp15 bears a hexa-histidine tag at the C-terminal end (underlined) in order to facilitate purification and to enable matrix-coupled refolding via a metal column (Ni, Zn, Cu).

```
KVEVEKVVDV AAAPAEQSAA QPSTASVDAA HNAQNSLDWA
GIYQGTLPAA DAGGIETELT LNADGTYALT EKYLDKEGEP
FASQGTFVWN EAGNIVTLQT GDQTGRQFMV GENTLSHLDM
EGKVIEGELA EFYVLSKQLE HHHHHH
```

SEQ ID NO. 3 shows EcSlyD-VcLp15 which is a fusion polypeptide according to the invention, comprising one molecule of *E. coli* SlyD as a chaperone and the mature VcLp15 sequence (26-163, underlined).

```
MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV EVEKVVDVAA
APAEQSAAQP STASVDAAHN AQNSLDWAGI YQGTLPAADA
GGIETELTLN ADGTYALTEK YLDKEGEPFA SQGTFVWNEA
GNIVTLQTGD QTGRQFMVGE NTLSHLDMEG KVIEGELAEF
YVLSKQLEHH HHHH
```

SEQ ID NO. 4 shows EcSkp-VcLp15 which is a fusion polypeptide according to the invention, comprising one molecule of *E. coli* Skp as a chaperone and the mature VcLp15 sequence (26-163, underlined).

```
MADKIAIVNM GSLFQQVAQK TGVSNTLENE FRGRASELQR
METDLQAKMK KLQSMKAGSD RTKLEKDVMA QRQTFAQKAQ
AFEQDRARRS NEERGKLVTR IQTAVKSVAN SQDIDLVVDA
NAVAYNSSDV KDITADVLKQ VKGGGSGGGS GGGSGGGSGG
GSGGGKVEVE KVVDVAAAPA EQSAAQPSTA SVDAAHNAQN
SLDWAGIYQG TLPAADAGGI ETELTLNADG TYALTEKYLD
KEGEPFASQG TFVWNEAGNI VTLQTGDQTG RQFMVGENTL
SHLDMEGKVI EGELAEFYVL SKQLEHHHHH H
```

SEQ ID NO. 5 shows the complete TpN17 sequence (amino acid residues 1-156) of *Treponema pallidum* as retrieved from the public database UniProt, accessible under UniProt ID P29722.

```
MKGSVRALCA FLGVGALGSA LCVSCTTVCP HAGKAKAEKV
ECALKGGIFR GTLPAADCPG IDTTVTFNAD GTAQKVELAL
EKKSAPSPLT YRGTWMVRED GIVELSLVSS EQSKAPHEKE
LYELIDSNSV RYMGAPGAGK PSKEMAPFYV LKKTKK
```

SEQ ID NO. 6 shows the TpN17 sequence as used in example 5. For this immunoassay, the mature TpN17 protein (amino acid residues 23-156) lacking the signal sequence (amino acid residues 1-22) was used. We found the four genuine cysteine residues of TpN17 to be dispensable for the antigenicity of the protein (data not shown). Thus, the cysteine residues at the positions 25, 29, 42 and 58 (numbering of the precursor protein) were replaced by alanine residues (underlined) in order to facilitate the refolding process and to suppress detrimental side reactions such as disulfide adduct formation.

```
VSATTVAPHA GKAKAEKVEA ALKGGIFRGT LPAADAPGID
TTVTFNADGT AQKVELALEK KSAPSPLTYR GTWMVREDGI
VELSLVSSEQ SKAPHEKELY ELIDSNSVRY MGAPGAGKPS
KEMAPFYVLK KTKK
```

SEQ ID NO. 7 shows the TpN17 sequence amino acid residues 23-156 (see also SEQ ID NO. 6) as used in fusion with different chaperone modules. TpN17 bears a hexa-histidine tag at the C-terminal end (underlined) in order to facilitate purification and to enable matrix-coupled refolding via a metal column (Ni, Zn, Cu). The N-terminal signal sequence of TpN17 (amino acid residues 1-22) was omitted in order to obtain the mature (processed) form of the protein in its native-like conformation.

```
VSATTVAPHA GKAKAEKVEA ALKGGIFRGT LPAADAPGID
TTVTFNADGT AQKVELALEK KSAPSPLTYR GTWMVREDGI
VELSLVSSEQ SKAPHEKELY ELIDSNSVRY MGAPGAGKPS
KEMAPFYVLK KTKKLEHHHH HH
```

SEQ ID NO. 8 shows the TpN17 sequence (underlined) to which two molecules of *E. coli* SlyD ("tandem SlyD") have been fused N-terminally; this molecule is also named EcSlyD-EcSlyD-TpN17 or EcSS-TpN17.

```
MKVAKDLVVS LAYQVRTEDG VLVDESPVSA PLDYLHGHGS
LISGLETALE GHEVGDKFDV AVGANDAYGQ YDENLVQRVP
KDVFMGVDEL QVGMRFLAET DQGPVPVEIT AVEDDHVVVD
GNHMLAGQNL KFNVEVVAIR EATEEELAHG HVHGAHDHHH
DHDHDGGGSG GGSGGGSGGG SGGGSGGGKV AKDLVVSLAY
QVRTEDGVLV DESPVSAPLD YLHGHGSLIS GLETALEGHE
VGDKFDVAVG ANDAYGQYDE NLVQRVPKDV FMGVDELQVG
MRFLAETDQG PVPVEITAVE DDHVVVDGNH MLAGQNLKFN
VEVVAIREAT EEELAHGHVH GAHDHHHDHD HDGGGSGGGS
GGGSGGGSGG GSGGGVSATT VAPHAGKAKA EKVEAALKGG
IFRGTLPAAD APGIDTTVTF NADGTAQKVE LALEKKSAPS
PLTYRGTWMV REDGIVELSL VSSEQSKAPH EKELYELIDS
NSVRYMGAPG AGKPSKEMAP FYVLKKTKKL EHHHHHH
```

SEQ ID NO. 9 shows the TpN17 sequence (underlined) to which two molecules of *Pasteurella multocida* SlyD ("tandem SlyD") have been fused N-terminally; this molecule is also named PmSlyD-PmSlyD-TpN17 or PmSS-TpN17.

```
MKIAKNVVVS IAYQVRTEDG VLVDEAPVNQ PLEYLQGHNN
LVIGLENALE GKAVGDKFEV RVKPEEAYGE YNENMVQRVP
KDVFQGVDEL VVGMRFIADT DIGPLPVVIT EVAENDVVVD
```

-continued

```
GNHMLAGQEL LFSVEVVATR EATLEEIAHG HIHQEGGGGS
GGGSGGGGGS GGGSGGGKIA KNVVVSIAYQ VRTEDGVLVD
EAPVNQPLEY LQGHNNLVIG LENALEGKAV GDKFEVRVKP
EEAYGEYNEN MVQRVPKDVF QGVDELVVGM RFIADTDIGP
LPVVITEVAE NDVVVDGNHM LAGQELLFSV EVVATREATL
EEIAHGHIHQ EGGGGSGGGS GGGSGGGSGG GSGGGVSATT
VAPHAGKAKA EKVEAALKGG IFRGTLPAAD APGIDTTVTF
NADGTAQKVE LALEKKSAPS PLTYRGTWMV REDGIVELSL
VSSEQSKAPH EKELYELIDS NSVRYMGAPG AGKPSKEMAP
FYVLKKTKKL EHHHHHH
```

SEQ ID NO. 10 shows the TpN17 sequence (underlined) to which one molecule of *E. coli* FkpA has been fused N-terminally; this molecule is also named EcFkpA-TpN17.

```
MAEAAKPATT ADSKAAFKND DQKSAYALGA SLGRYMENSL
KEQEKLGIKL DKDQLIAGVQ DAFADKSKLS DQEIEQTLQA
FEARVKSSAQ AKMEKDAADN EAKGKEYREK FAKEKGVKTS
STGLVYQVVE AGKGEAPKDS DTVVVNYKGT LIDGKEFDNS
YTRGEPLSFR LDGVIPGWTE GLKNIKKGGK IKLVIPPELA
YGKAGVPGIP PNSTLVFDVE LLDVKPAPKA DAKPEADAKA
ADSAKKGGGS GGGSGGGSGG GSGGGSGGGV SATTVAPHAG
KAKAEKVEAA LKGGIFRGTL PAADAPGIDT TVTFNADGTA
QKVELALEKK SAPSPLTYRG TWMVREDGIV ELSLVSSEQS
KAPHEKELYE LIDSNSVRYM GAPGAGKPSK EMAPFYVLKK
TKKLEHHHHH H
```

SEQ ID NO. 11 shows the TpN17 sequence (underlined) to which one molecule of *E. coli* Skp has been fused N-terminally; this molecule is also named EcSkp-TpN17.

```
MADKIAIVNM GSLFQQVAQK TGVSNTLENE FRGRASELQR
METDLQAKMK KLQSMKAGSD RTKLEKDVMA QRQTFAQKAQ
AFEQDRARRS NEERGKLVTR IQTAVKSVAN SQDIDLVVDA
NAVAYNSSDV KDITADVLKQ VKGGGSGGGS GGGSGGGSGG
GSGGGVSATT VAPHAGKAKA EKVEAALKGG IFRGTLPAAD
APGIDTTVTF NADGTAQKVE LALEKKSAPS PLTYRGTWMV
REDGIVELSL VSSEQSKAPH EKELYELIDS NSVRYMGAPG
AGKPSKEMAP FYVLKKTKKL EHHHHHH
```

SEQ ID NO. 12 shows the amino acid sequence of the glycine-rich spacer (comprising triple glycine units separated by a serine) that can be used as a flexible, soluble and protease-resistant spacer or linker between several chaperone moieties.

```
GGGSGGGSGG GSGGGSGGGS GGG
```

DETAILED DESCRIPTION OF THE INVENTION

Immunoassays for the detection of antibodies against *Treponema pallidum* tend to show false positive results as could be demonstrated by the inventors. In particular when the *Treponema* antigen TpN17 is used, the number of false positive signals is significantly elevated. This phenomenon has been observed with human sera that had definitely been characterized as anti-*Treponema* negative: when using the TpN17 antigen, a significant number of false positives were found (see example 5). Yet, TpN17 is a crucial immunogen in *Treponema* infections and a paramount antigen in syphilis serology. As a consequence, it is not a viable option to circumvent this interference problem by simply omitting the TpN17 antigen.

We therefore started out with the design of a recombinant TpN17 variant which enables the reliable and sensitive detection of anti-TpN17 antibodies. More precisely, we fused TpN17 to a solubility-conferring chaperone (tandem SlyD, namely EcSlyD-EcSlyD and PmSlyD-PmSlyD) via a flexible linker rich in glycine and serine residues. Due to the beneficial effects of the fused folding helpers, the resulting fusion polypeptide meets all the physicochemical and immunological requirements of a good antigen for serological purposes (i.e. for use in an immunoassay).

The chaperone-TpN17 fusion proteins that we designed for an automated syphilis immunoassay are highly soluble and reactive and are advantageously used in a double antigen sandwich format. As mentioned above, during the feasibility studies for a syphilis immunoassay it turned out that TpN17 is indeed an immunodominant *Treponema* antigen with outstanding diagnostic significance. In other words, it is imperative to use a TpN17 variant in a Syphilis immunoassay in order to warrant the desired sensitivity. Yet, when chaperone polypeptide fusion constructs of TpN17 were used in the double antigen sandwich (DAGS) format, the problem became evident: even though the TpN17 fusion constructs had been designed in an asymmetric fashion (i.e., the symmetry of the DAGS format was deliberately abolished by the use of different fusion partners on the biotin side and the ruthenium side), and despite the use of chaperone polymers as anti-interference additives, quite a number of positive results occurred in a panel of well-characterized anti-*Treponema* negative human sera, leading to a substantial worsening of the assay specificity. Obviously, some of the anti-*Treponema* negative human sera contained at least one unknown factor which was able to interact specifically with the TpN17 antigen.

To our surprise, it turned out that addition of recombinant-derived protein Lp15 from the human pathogen *Vibrio cholerae* (VcLp15)—which is, despite certain sequence homologies, an organism quite unrelated to *Treponema pallidum*—to the immunoassay mixture reduced the elevated signals of the false positives to the signal level of negative sera as can be seen in example 5 and tables 2-5. We conclude that VcLp15 (when added in an unlabeled form) is able to recognize, bind and quench the unknown interference factor(s) which are directed towards TpN17. It has indeed turned out that VcLp15 is an invaluable tool for reducing false positive results and for improving the specificity of syphilis immunoassays based on the *Treponema* antigen TpN17.

In detail, the current invention relates to a method for detecting antibodies against the TpN17 antigen of *Treponema pallidum* in an isolated sample wherein a peptide sequence of *Vibrio cholerae* lipoprotein 15 (VcLp15) or a partial sequence thereof is used as a reagent for reduction of interference and for minimizing false positive results.

Any TpN17 antigen or variant thereof can be used provided that the antigen's conformation is native-like enough to be recognized by the antibodies present in the sample. In its natural host, *T. pallidum*, the N-terminal signal sequence of TpN17 (residues 1-22) is cleaved off the precursor protein to allow folding of the mature TpN17 part into its native conformation. In other words, the signal sequence is dispensable when TpN17 is produced recombinantly in a prokaryotic host such as *E. coli*. It rather impedes proper folding of the target molecule and is thus omitted. In some embodiments, a peptide sequence according to UniProt ID P29722 (SEQ ID NO. 5) or SEQ ID NO. 6 or a partial sequence of SEQ ID NOs. 5 or 6 is used. The partial sequence comprises at least about 100 amino acids of SEQ ID NOs 5 or 6. Another useful sequence is an amino acid sequence comprising amino acid residues 23-156 of SEQ ID NO. 5 or amino acid residues 1-134 of SEQ ID NO. 6.

A useful TpN17 antigen is a polypeptide according to SEQ ID NOs. 7 to 11 wherein TpN17 has been fused to various chaperone peptide sequences. To facilitate the refolding process after purification and to suppress disulfide adduct formation the cysteine residues in all envisaged TpN17 antibodies may be replaced by other amino acid residues such as alanine or serine. These residues replace the oxidation-sensitive thiol moiety of the cysteine side chain but almost equal the cysteine residue in size. Therefore, they usually fit into the overall three-dimensional protein structure and do not severely compromise folding and stability of the cysteine-free protein variant.

According to the method of the current invention a peptide sequence of *Vibrio cholerae* lipoprotein 15 (VcLp15) or a partial sequence thereof is used as a reagent for reduction of interference, i.e. for minimizing false positive results. In some embodiments said partial sequence of VcLp15 comprises amino acids comprises amino acid residues 26-163 of SEQ ID NOs. 1 or 2. The N-terminal signal sequence comprising residues 1-25 of SEQ ID NO. 1 is dispensable. In a further mode of the invention said VcLp15 partial sequence of amino acid residues 26-163 of SEQ ID NOs. 1 or 2 can be truncated by 1 to 5 amino acids at its N-terminal or C-terminal end or at both ends. In another embodiment said VcLp15 partial sequence of amino acid residues 26-163 of SEQ ID NOs. 1 or 2 can be modified in such a way that conservative amino acid substitutions can be introduced like e.g. substitution of an alanine residue by a serine residue or cysteine. Any of these three amine acids can be replaced by the other two amino acids. Other examples of conservative amino acid substitutions known by a person skilled in the art are Serin/Cystein/Alanin, Isoleucin/Valin or Phenylalanin/Tyrosin. For any of these modifications it is important that the three-dimensional structure of the *Vibrio cholerae* lipoprotein 15 (VcLp15) remains unchanged.

In some embodiments, the VcLp15 peptide sequence or partial sequence thereof used in the above-described method is fused to a chaperone to provide high expression yields and to facilitate the refolding process after purification.

A further aspect of the invention is a fusion polypeptide comprising a VcLp15 peptide sequence according to SEQ ID NO. 1 or 2 or a partial sequence of SEQ ID NOs. 1 or 2 and a chaperone.

The use of polypeptide fusion proteins wherein chaperones are fused to difficult target antigen sequences to solubilize them and make them more benign is well-known in the art and has been described in great detail before such as in the international patent application WO 2003/000878. Known and well-documented examples of useful fusion chaperones are SlyD, FkpA, Skp and SlpA, see also European Patent Application EP2127678A1.

A further aspect of the invention therefore is a fusion polypeptide comprising a VcLp15 peptide sequence and a chaperone. In certain embodiments the chaperone is selected from the group consisting of SlyD, SlpA, FkpA and Skp. These chaperones may originate from various organisms, and in certain embodiments the chaperone sequences are derived from *E. coli.*

In another embodiment of the invention the fusion polypeptide comprising a VcLp15 peptide sequence comprises SEQ ID NO. 3 (EcSlyD-VcLp15).

The use of a fusion polypeptide comprising a VcLp15 peptide sequence and a chaperone as an additive in an immunoassay for reduction of interferences and for minimizing false positive results is also an aspect of the current invention.

Another aspect of the invention is a reagent kit for the detection of antibodies against *Treponema pallidum* antigens in an isolated sample by an immunoassay, comprising a TpN17 antigen and a fusion polypeptide comprising a VcLp15 peptide sequence and a chaperone as described in detail further above.

Moreover, the invention covers a method for detecting antibodies against the TpN17 antigen of *Treponema pallidum* in an isolated sample, said method comprising the steps of a) forming an immunoreaction admixture by admixing a body fluid sample with a specific binding partner that can be specifically bound by said antibodies present in said sample b) adding a fusion polypeptide comprising a VcLp15 peptide sequence as defined above to said immunoreaction admixture either before, at the same time or after said specific binding partner is added to said sample c) maintaining said immunoreaction admixture for a time period sufficient for allowing the antibodies present in said body fluid sample to immunoreact with said specific binding partner to form an immunoreaction product; and d) detecting the presence and/or the concentration of any of said immunoreaction product.

The fusion polypeptide of the invention can be added to the immunoassay admixture (comprising sample and a binding partner specifically binding to the analyte antibodies in the sample) either before, at the same time or after said specific binding partner is added to the sample. In some embodiments, the fusion polypeptide is added to the test reagents before the body fluid sample containing the analyte antibodies, is brought into contact with the specific binding partners.

In one embodiment of the invention the immunoassay for detecting anti-*Treponema* antibodies in an isolated sample is performed according to the so-called double antigen sandwich concept (DAGS). Sometimes this assay concept is also termed double antigen bridge concept, because the two antigens are bridged by an antibody analyte. In such an assay the ability of an antibody to bind at least two different molecules of a given antigen with its two (IgG, IgE), four (IgA) or ten/twelve (IgM) paratopes is required and used.

In more detail, an immunoassay for the determination of anti-*Treponema* antibodies according to the double antigen bridge format is carried out by incubating a sample containing the anti-*Treponema* antibodies with two different TpN17 antigens, i.e. a first ("solid phase") TpN17 antigen and a second ("detection") TpN17 antigen, wherein each of the said antigens binds specifically to said anti-*Treponema* antibodies. The first antigen is or can be bound directly or indirectly to a solid phase and usually carries an effector group which is part of a bioaffine binding pair like biotin/avidin. For example, if the first antigen is conjugated to biotin the solid phase is coated with either avidin or streptavidin. The second antigen carries a detectable label. Then an immunoreaction admixture is formed comprising the first antigen, the sample antibody and the second antigen. A solid phase to which the first antigen can be bound is added either before the addition of the sample to said antigens or after the immunoreaction admixture is formed. This immunoreaction admixture is maintained for a time period sufficient for allowing anti-*Treponema* antibodies against said TpN17 antigens in the body fluid sample to immunoreact with said TpN17 antigens to form an immunoreaction product. Next step is a separation step wherein the liquid phase is separated from the solid phase. Finally, the presence of any of said immunoreaction product is detected in the solid or liquid phase or both.

In said DAGS immunoassay the basic structures of the "solid phase antigen" and the "detection antigen" are the same. It is also possible to use similar but different TpN17 antigens, which are immunologically cross-reactive in a double antigen bridge assay. The essential requirement for performing such assays is that the relevant epitope or the relevant epitopes are present on both antigens. According to the invention it is desirable to use different fusion moieties for each TpN17 antigen (e.g. EcFkpA is fused to TpN17 on the solid phase side and EcSkp is fused to TpN17 on the detection side) as such variations break the symmetry of the DAGS format and thus reduce the problem of antibody-mediated bridging of the fusion chaperones which would lead to a false positive outcome of the immunoassay. In brief, the use of structurally distant fusion partners on both sides of a DAGS format reduces unwanted immunological cross-reactions and thus improves specificity.

The current invention therefore also relates to a method for detecting antibodies against the TpN17 antigen of *Treponema pallidum* in an isolated sample wherein a peptide sequence of VcLp15 is used as a reagent for reduction of interference and for minimizing false positive results. Said method is further characterized in that the assay is carried out in the double-antigen sandwich format (DAGS). Moreover, said assay uses two TpN17 antigen fusion polypeptides—a first and a second TpN17 antigen—wherein both TpN17 antigens are identical or at least immunologically cross-reactive against the same antibodies so that a bridging between both antigens by the antibodies present in the sample is possible. In addition, the first and the second antigens are fused to different chaperones as described in the preceding paragraph.

Moreover, the use of specific chaperone fusion partners like Skp and FkpA may facilitate a considerably improved IgM recognition and detection. Due to their avidity mode of binding, IgM molecules can only react with polymeric antigens possessing a medium to high epitope density. Both Skp and FkpA are oligomeric chaperones serving a role as folding helpers in the periplasm of Gram negative bacteria. To our surprise, we find that the quartery structure of Skp and FkpA is maintained when large target molecules are fused to the C-termini of the chaperones. As a consequence, the FkpA-TpN17 and Skp-TpN17 fusion proteins reproducibly form natural oligomers with defined epitope densities that are sufficient to detect IgM molecules. Sensitive and specific IgM detection is a very important feature warranting reliable detection of early and primary syphilis infections. Since we aim at developing an immunoassay for total immunoglobulin detection (i.e. the detection of both IgG and IgM), the oligomeric antigen modules FkpA-TpN17 and Skp-TpN17 may be used advantageously as specifiers on both sides of a DAGS format (e.g. FkpA-TpN17-biotin and Skp-TpN17-ruthenium). Since FkpA and Skp are very distinct from each other in terms of structure, the risk of unwanted immunological cross-reaction and bridging via the fusion partners is very low. It is further reduced by adding chemically polymerized FkpA and Skp anti-interference additives to the assay.

Various additional formats and principles of immunoassays for detecting analytes and different modes of detection have been widely described and are familiar to a person skilled in the art.

According to the invention any biological isolated sample in which *Treponema* antibodies might be detectable can be used. In particular human blood, serum, plasma or saliva are suitable as sample material.

The invention is further illustrated in the examples section.

Example 1

Cloning and Purification of TpN17 and VcLp15 Chaperone Fusion Polypeptides

Cloning of Expression Cassettes

On the basis of the pET24a expression plasmid of Novagen (Madison, Wis., USA), expression cassettes encoding TpN17 and VcLp15 fusion proteins were obtained essentially as described (Scholz, C. et al., J. Mol. Biol. (2005) 345, 1229-1241). The sequences of the TpN17 and VcLp15 antigens were retrieved from the SwissProt database (SwissProt ID P29722 and Q9KQN6, respectively). A synthetic gene encoding mature TpN17 aa 23-156 (the signal peptide spanning amino acid residues 1-22 was omitted) with a glycine-rich linker region fused in frame to the N-terminus was purchased from Medigenomix (Martinsried, Germany). The cysteine residues of TpN17 at positions 25, 29, 42 and 58 were changed to alanine residues in order to prevent unwanted side-effects such as oxidation or intermolecular disulfide bridging. BamHI and XhoI restriction sites were at the 5' and the 3' ends of the TpN17-coding region, respectively. A further synthetic gene encoding two EcSlyD units (residues 1-165 according to SEQ ID NO. 1, SwissProt accession no. P0A9K9) connected via a glycine-rich linker region and encompassing part of a further linker region at the C-terminus were likewise purchased from Medigenomix. NdeI and BamHI restriction sites were at the 5' and 3' ends of this cassette, respectively. The genes and the restriction sites were designed to enable the in frame fusion of the chaperone part EcSlyD-EcSlyD and the TpN17 antigen part by simple ligation. In order to avoid inadvertent recombination processes and to increase the genetic stability of the expression cassette in the *E. coli* host, the nucleotide sequences encoding the EcSlyD units were degenerated as were the nucleotide sequences encoding the extended linker regions. i.e., different codon combinations were used to encode identical amino acid sequences.

The pET24a vector was digested with NdeI and XhoI and the cassette comprising tandem-SlyD fused in frame to *Treponema* TpN17 23-156 was inserted. Expression cassettes comprising *Pasteurella multocida* SlyD (1-156, SwissProt ID Q9CKP2) or *E. coli* Skp (21-161, SwissProt ID P0AEU7) or FkpA (26-270, SwissProt ID P45523) were constructed accordingly, as well as expression cassettes comprising target polypeptides different from TpN17, notably the *Vibrio cholerae* lipoprotein Lp15 (26-163, SwissProt ID Q9KQN6). As with TpN17, the genuine cysteine residues of VcLp15 at positions 74 and 77 (precursor Lp15 numbering) were changed to alanine residues in order to prevent unwanted side-effects such as oxidation or intermolecular disulfide bridging. All recombinant fusion polypeptide variants contained a C-terminal hexahistidine tag to facilitate Ni-NTA-assisted purification and refolding. QuikChange (Stratagene, La Jolla, Calif., USA) and standard PCR techniques were used to generate point mutations, deletion, insertion and extension variants or restriction sites in the respective expression cassettes.

The drawing below shows a scheme of the *Treponema* TpN17 full length antigen 23-156 bearing two SlyD chaperone units fused in frame to its N-terminal end. To denote the *E. coli* origin of the SlyD fusion partner, the depicted fusion polypeptide has been named EcSlyD-EcSlyD-TpN17 (23-156); see also SEQ ID NO. 8.

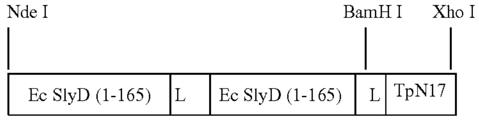

L = $(GGGS)_5$GGG-Linker

The insert of the resulting plasmid was sequenced and found to encode the desired fusion protein. The complete amino acid sequence of the TpN17 and VcLp15 fusion polypeptides is shown in SEQ ID NOs. 2 to 4 (VcLp15) and 7 to 11 (TpN17). The amino acid sequence of the linker L is shown is SEQ ID NO. 12.

Purification of Fusion Proteins Comprising TpN17 or VcLp15

All TpN17 and VcLp15 fusion protein variants were purified by using virtually identical protocols. *E. coli* BL21 (DE3) cells harboring the particular pET24a expression plasmid were grown at 37° C. in LB medium plus kanamycin (30 μg/ml) to an $OD_{600}$ of 1.5, and cytosolic overexpression was induced by adding 1 mM isopropyl-β-D-thiogalactoside. Three hours after induction, cells were harvested by centrifugation (20 min at 5000 g), frozen and stored at −20° C. For cell lysis, the frozen pellet was resuspended in chilled 50 mM sodium phosphate pH 8.0, 7.0 M GdmCl, 5 mM imidazole and the suspension was stirred for 2 h on ice to complete cell lysis. After centrifugation and filtration (0.45 μm/0.2 μm), the crude lysate was applied onto a Ni-NTA column equilibrated with the lysis buffer including 5.0 mM TCEP. The subsequent washing step was tailored for the respective target protein and ranged from 5 to 15 mM imidazole (in 50 mM sodium phosphate pH 8.0, 7.0 M GdmCl, 5.0 mM TCEP). At least 10-15 volumes of the washing buffer were applied. Then, the GdmCl solution was replaced by 50 mM potassium phosphate pH 8.0, 100 mM KCl, 10 mM imidazole, 5.0 mM TCEP to induce conformational refolding of the matrix-bound protein. In order to avoid reactivation of copurifying proteases, a protease inhibitor cocktail (Complete® EDTA-free, Roche) was included in the refolding buffer. A total of 15-20 column volumes of refolding buffer were applied in an overnight reaction. Then, both TCEP and the Complete® EDTA-free inhibitor cocktail were removed by washing with 3-5 column volumes 50 mM potassium phosphate pH 8.0, 100 mM KCl, 10 mM imidazole. Subsequently, the imidazole concentration—still in 50 mM potassium phosphate pH 8.0, 100 mM KCl—was raised to 25-50 mM (depending on the respective target protein) in order to remove unspecifically bound protein contaminants. The native protein was then eluted by 500 mM imidazole in the same buffer. Protein-containing fractions were assessed for purity by Tricine-SDS-PAGE and pooled. Finally, the proteins were subjected to size-exclusion-chromatography (Superdex HiLoad, Amersham Pharmacia) and the protein-containing fractions were pooled and concentrated to 10-20 mg/ml in an Amicon cell (YM10).

After the coupled purification and refolding protocol, protein yields of roughly 10-30 mg could be obtained from 1 g of *E. coli* wet cells, depending on the respective target protein.

Example 2

Spectroscopic Measurements

Protein concentration measurements were performed with an Uvikon XL double-beam spectrophotometer. The molar extinction coefficients ($\epsilon_{280}$) were determined by using the procedure described by Pace (1995), Protein Sci. 4, 2411-2423. The molar extinction coefficients ($\epsilon_{M280}$) used for the distinct fusion polypeptides are specified in table 1.

TABLE 1

Protein parameters of the fusion polypeptide variants used in this study. All parameters are referring to the respective protein monomers.

| fusion protein | length of target protein (aa residues) | molecular weight of fusion polypeptide (Da) | pI | $\epsilon_{M280}$ $M^{-1}cm^{-1}$ | $Abs_{0.1\%}$ (=1 mg/ml) |
|---|---|---|---|---|---|
| | TpN17 variants | | | | |
| EcSlyD-EcSlyD-TpN17 | 23-156 | 54048 | 5.0 | 23380 | 0.433 |
| PmSlyD-PmSlyD-TpN17 | 23-156 | 52171 | 4.9 | 23380 | 0.448 |
| EcFkpA-TpN17 | 23-156 | 42995 | 8.3 | 27390 | 0.637 |
| EcSkp-TpN17 | 23-156 | 32461 | 9.3 | 12950 | 0.399 |
| | VcLp15 variants | | | | |
| EcSlyD-VcLp15 | 26-163 | 35156 | 4.6 | 22920 | 0.652 |
| EcSkp-VcLp15 | 26-163 | 33010 | 5.3 | 18450 | 0.559 |

The amino acid sequences of the fusion polypeptide variants are shown in SEQ ID NOs. 3, 4, 8, 9, 10 and 11, respectively.

Example 3

Coupling of Biotin and Ruthenium Moieties to the TpN17 Fusion Proteins

The lysine ε-amino groups of the TpN17 fusion polypeptides were modified at protein concentrations of 10-30 mg/ml with N-hydroxy-succinimide activated biotin and ruthenium label molecules, respectively. The label/protein ratio varied from 2:1 to 5:1 (mol:mol), depending on the respective fusion protein. The reaction buffer was 150 mM potassium phosphate pH 8.0, 100 mM KCl, 0.5 mM EDTA. The reaction was carried out at room temperature for 15 mM and stopped by adding buffered L-lysine to a final concentration of 10 mM. To avoid hydrolytic inactivation of the labels, the respective stock solutions were prepared in dried DMSO (seccosoiv quality, Merck, Germany). DMSO concentrations up to 25% in the reaction buffer were well tolerated by all fusion proteins studied. After the coupling reaction, unreacted free label was removed by passing the crude protein conjugate over a gel filtration column (Superdex 200 HiLoad).

Example 4

CD-Detected Thermally Induced Unfolding of EcSlyD-VcLp15

Near-UV CD spectra were recorded with a Jasco-720 spectropolarimeter with a thermostatted cell holder and were converted to mean residue ellipticity. The buffer was 50 mM potassium phosphate pH 7.0, 250 mM KCl, 0.5 mM EDTA. The pathlength was 0.2 cm, the protein concentration was ~74 μM (2.6 mg/ml). The measuring range was 250-330 nm, the band width was 1.0 nm, the scanning speed was 20 nm/min at a resolution of 0.5 nm, and the response was 1 s. In order to improve the signal-to-noise ratio, spectra were measured nine times and averaged.

Circular dichroism spectroscopy (CD) is the method of choice to assess both the secondary and the tertiary structure of proteins. Ellipticity in the aromatic region (260-320 nm) reports on tertiary contacts within a protein (i.e., the globular structure of a regularly folded protein) and is considered as the fingerprint region of a native-like fold (conformation).

Near UV CD spectra of EcSlyD-VcLp15 were monitored to address the question whether the fusion protein adopts an ordered conformation after the matrix-coupled refolding procedure which is the crucial step in the purification process. The answer is quite clear-cut: the near UV CD signal of EcSlyD-VcLp15 unequivocally reports an orderly tertiary structure of the fusion polypeptide. The aromatic residues of EcSlyD-VcLp15 are obviously embedded in the lipophilic protein core and thus experience asymmetric surroundings which strongly points to a native-like conformation of both EcSlyD and VcLp15 within the fusion construct (FIG. 1).

In order to address the question whether the thermally induced unfolding of EcSlyD-VcLp15 is reversible, melting curves were monitored in the near UV region at a detection wavelength of 281 nm. The temperature range was 20-80° C., the band width was 1.0 nm, the temperature ramp was 1° C./min and the response was 4 s (see FIG. 2).

Figure 2:
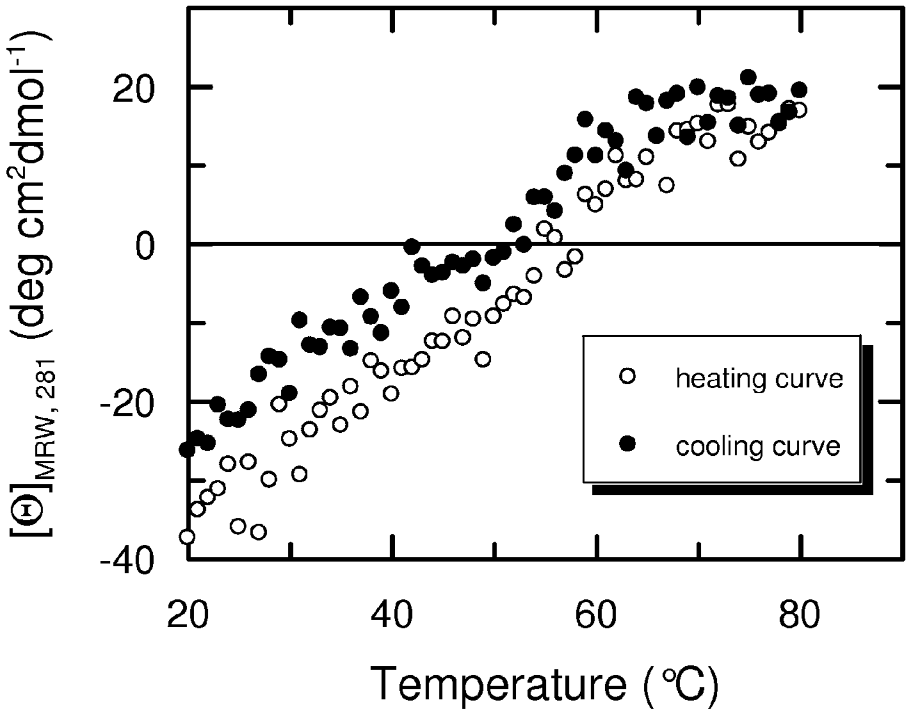
FIG. 2 shows melting curves of the fusion polypeptide EcSlyD-VcLp15 according to the invention, as monitored by CD-spectroscopy in the near UV region. For details refer to example 4.

The thermally-induced unfolding was monitored at 281 nm (which is the wavelength of the maximal signal amplitude for EcSlyD-VcLp15). Upon heating, the non-covalent contacts which stabilize the native conformation of the EcSlyD-VcLp15 molecule become loose and finally break down. This thermally induced unfolding is reflected in an increase in the CD signal as shown in FIG. 2. At 80° C., EcSlyD-VcLp15 is fully unfolded. Strikingly, the native-like CD signal is restored again when the protein solution is chilled down to 20° C. Despite a slight hysteresis, the unfolding curve and the refolding curve virtually superimpose, strongly indicative of a reversible refolding behavior of EcSlyD-VcLp15. It must be admitted that the cooperativity of unfolding is rather low and that the typical sigmoidal shape of a protein melting curve is not observed in the case of EcSlyD-VcLp15. Yet, we unambiguously find that EcSlyD-VcLp15 is able to readopt its native-like conformation when the protein solution is chilled from 80° C. to 20° C. Indeed, the near UV CD spectra monitored prior to and after the thermally induced unfolding, virtually superimpose (see FIG. 1). In conclusion, EcSlyD-VcLp15 possesses robust folding properties which are outstanding for a fusion polypeptide and which are highly desired for a molecule that serves as an anti-interference additive in an immunoassay. These benign physicochemical properties, in combination with an outstanding solubility (>130 mg/ml in phosphate-buffered saline) and the anti-interference potential in an anti-*Treponema* immunoassay makes EcSlyD-VcLp15 a very attractive molecule warranting a high specificity in syphilis serology.

Example 5

Anti-Interference Activity of *Vibrio cholerae* Lp15 in a Syphilis Immunoassay

The anti-interference activity of the polypeptide fusion variants of *Vibrio cholerae* Lp15 was assessed in an automated Elecsys® 2010 analyzer (Roche Diagnostics GmbH). Elecsys® is a registered trademark of the Roche group. Measurements were carried out in the double antigen sandwich format.

Signal detection in Elecsys® 2010 is based on electrochemiluminescence. The biotin-conjugate (i.e. the capture-antigen) is immobilized on the surface of a streptavidin coated magnetic bead whereas the detection-antigen bears a complexed Ruthenium cation (switching between the redox states 2+ and 3+) as the signaling moiety. In the presence of a specific immunoglobulin analyte, the chromogenic ruthenium complex is bridged to the solid phase and emits light at 620 nm after excitation at a platinum electrode. The signal output is in arbitrary light units.

The recombinant anti-interference Lp15 polypeptides were assessed in a double antigen sandwich (DAGS) immunoassay format. To this end, recombinant *Treponema* antigen TpN17 was used as a biotin and a ruthenium conjugate, respectively, to detect anti-TpN17 antibodies in human sera. TpN17 is one of the immunodominant antigens of *Treponema pallidum*, and soluble variants of TpN17—as disclosed in this patent application—are invaluable tools for the detection of syphilis infections. In order to detect anti-TpN17 IgG molecules, EcSlyD-EcSlyD-TpN17-biotin and PmSlyD-PmSlyD-TpN17-ruthenium were used in R1 (reagent buffer 1) and R2 (reagent buffer 2), respectively. In order to detect both anti-TpN17 IgM and IgG molecules, EcFkpA-TpN17-biotin and EcSkp-TpN17-ruthenium were used in R1 (reagent buffer 1) and R2 (reagent buffer 2), respectively. The concentrations of the antigen conjugates in R1 and R2, respectively, were 200 ng/ml each.

In a first experiment, human sera negative for *Treponema* were assessed with the aforementioned DAGS immunoassay setup. In order to get a hint to the incidence rate of false positives which are solely targeted to the TpN17 moiety, the screening was performed in the presence of SS-Helix (GDA, P), a GDA-crosslinked soluble heterogeneous SlyD polymer which is customarily used as an anti-interference substance. In addition, EcSkp-EcSlyD-EcSlyD, another anti-interference module, was included in the assay buffer in order to rule out interference phenomena due to moieties different from the very TpN17 part. SS-Helix (GDA,P) and EcSkp-EcSlyD-EcSlyD were added to R1 (reagent 1 buffer containing the biotin conjugate) in large excess amounts (10 μg/ml). 75 μl R1 (reagent 1 buffer, biotin conjugate and anti-interference polymers), 75 μl R2 (reagent 2 buffer, ruthenium conjugate), 10 μl sample (human serum) and 40 μl bead suspension are then mixed and incubated to yield a reaction volume of roughly 200 μl.

By means of this approach, approximately 8 human sera could be found (out of ~2500 negative human sera) which clearly were negative for anti-*Treponema pallidum* antibodies but exhibited elevated signals in the DAGS format when using TpN17 as an antigen. Elecsys® signals were, however, not increased when other *Treponema* antigens such as TpN15 or TpN47 were used instead of TpN17 (data not shown). This finding points to a specific anti-TpN17 interference factor.

Table 2 illustrates the anti-interference effect of unlabeled monomeric EcSlyD-VcLp15 in an oligomeric TpN17 assay setup. EcFkpA-TpN17-Bi(DDS) and EcSkp-TpN17-BPRu (SK(2)DSS) were used as oligomeric detection antigens, and unlabeled EcSlyD-VcLp15 was added to R1 in increasing concentrations. It is obvious that the signals of the true positive sera are significantly quenched upon addition of Lp15. Yet, the positive signals clearly remain positive, even when VcLp15 is added in high concentrations such as 1 μg/ml to R1. As expected, well-characterized human sera (Trina Bioreactives AG, Nänikon, Switzerland) for which *Treponema* infections have clearly been ruled out, exhibit very low signals close to the system-inherent background signal (~450 counts), irrespective of the addition of VcLp15. Interference sera such as C131839, C132663, C132723, R183554 and C132976 exhibit significantly elevated signals when no VcLp15 anti-interference module is added. Since the averaged signal of the negative sera amounts to ~770 counts, it is evident that signal levels of 15,146 counts (for human serum C132663) or 8,503 counts (for human serum C132723) would point to a true positive result raising the suspicion of a syphilis infection. It is remarkable that addition of VcLp15 at a concentration of 1.0 μg/ml in R1 reduces the elevated signals to the normal background signal level, revealing the putatively positive results as false positive. The same holds true when unlabeled monomeric EcSlyD-VcLp15 is added in a monomeric TpN17 DAGS setup (Tab. 3). Again, significantly elevated signal levels as with human serum C132663 are reduced from 11,128 counts to 651 counts when EcSlyD-VcLp15 is added to R1 at a concentration of 1.0 μg/ml. Conversely, oligomeric VcLp15 (EcSkp-VcLp15) efficiently quenches elevated and false positive signals, respectively, to the negative signal background both in the oligomeric (Tab. 4) and in the monomeric (Tab. 5) TpN17 DAGS setup.

TpN17 from *Treponema pallidum* and lipoprotein 15 from *Vibrio cholerae* share 34% sequence identity and 55% homology over a stretch of 97 amino acid residues. It is probably via this shared sequence (and probably structural) motif that the immunological cross-reaction takes place, evoking high signals and thus pretending a positive outcome in *Treponema* assays that are based on TpN17 antigen. Addition of the VcLp15 anti-interference protein to the assay mixture reduces the elevated signals to normal negatives, as shown in Tab. 2-5. The disclosed data provide compelling evidence that even very strong interferences, i.e. high false positives, may be efficiently eliminated by addition of *Vibrio cholerae* lipoprotein 15, in a monomeric or oligomeric form. The bottom line of the results shown in tables 2-5 is the following: interferences due to the use of recombinant TpN17 antigen in a DAGS immunoassay are rather frequent (>1 in 500 negative sera) and they can efficiently be mitigated by the addition of lipoprotein 15 from *Vibrio cholerae*, which is a bacterial genus phylogenetically rather distant from *Treponema pallidum*. Put simply, this application discloses that the addition of an easily available recombinant protein significantly improves the specificity of a TpN17-based Syphilis immunoassay for the detection of anti-*Treponema* antibodies.

TABLE 2

| Oligomeric TpN17; addition of monomeric VcLp15 | | | | | | | |
|---|---|---|---|---|---|---|---|
| | | EcSlyD-VcLp15 | | | | | |
| R1<br>c (μg/ml) | | 0<br>counts | 0.1<br>counts | 0.2<br>counts | 0.3<br>counts | 0.5<br>counts | 1.0<br>counts |
| positive sera | | | | | | | |
| PLTP_124 | undil. | 1,274,726 | 1,171,468 | 1,166,110 | 1,092,657 | 973,974 | 793,911 |
| PLTP_124 | 1:50 | 154,146 | 156,165 | 136,898 | 131,248 | 101,395 | 62,840 |
| PLTP_121 | 1:50 | 223,230 | 211,697 | 205,298 | 190,606 | 151,374 | 93,737 |
| PLTP_121 | 1:100 | 112,031 | 105,466 | 103,909 | 91,727 | 72,926 | 47,972 |
| BM 146027 | SC_056 | 1,408,728 | 1,357,227 | 1,258,085 | 1,217,480 | 1,149,624 | 1,133,749 |
| BM 146623 | SC_058 | 1,187,013 | 1,158,037 | 1,083,204 | 1,083,952 | 1,078,868 | 1,050,374 |
| negative sera | | | | | | | |
| Trina #0642 | neg. | 778 | 716 | 722 | 698 | 698 | 661 |
| Trina #0645 | neg. | 725 | 703 | 722 | 682 | 715 | 706 |
| Trina #0646 | neg. | 797 | 795 | 817 | 802 | 784 | 784 |
| Trina #0647 | neg. | 774 | 786 | 764 | 773 | 762 | 742 |
| interference sera | | | | | | | |
| C131839 | false positive | 5,795 | 5,090 | 4,464 | 3,861 | 2,851 | 1,555 |
| C132663 | false positive | 15,146 | 2,116 | 1,110 | 878 | 765 | 724 |
| C132723 | false positive | 8,503 | 7,725 | 6,811 | 5,357 | 2,298 | 941 |
| R183554 | false positive | 11,072 | 10,030 | 9,142 | 7,413 | 4,488 | 2,534 |
| C132976 | false positive | 5,687 | 5,174 | 4,446 | 3,690 | 2,509 | 1,419 |

R1 EcFkpA-TpN17-Bi(DDS)
R2 EcSkp-TpN17-BPRu(SK(2)DSS)

TABLE 3

| Monomeric TpN17; addition of monomeric VcLp15 | | | | | | | |
|---|---|---|---|---|---|---|---|
| | | EcSlyD-VcLp15 | | | | | |
| R1<br>c (μg/ml) | | 0<br>counts | 0.1<br>counts | 0.2<br>counts | 0.3<br>counts | 0.5<br>counts | 1.0<br>counts |
| positive sera | | | | | | | |
| PLTP_124 | undil. | 1,467,523 | 1,374,990 | 1,272,604 | 1,272,720 | 1,208,354 | 1,164,404 |
| PLTP_124 | 1:50 | 167,294 | 155,940 | 153,077 | 136,428 | 124,244 | 89,204 |
| BM 146624 | undil. | 1,451,271 | 1,423,730 | 1,376,393 | 1,359,799 | 1,370,884 | 1,369,198 |
| BM 146624 | 1:10 | 436,534 | 403,003 | 384,434 | 365,742 | 329,370 | 259,984 |
| BM 145855 | SC_055 | 901,047 | 816,640 | 766,258 | 707,030 | 616,574 | 511,011 |
| BM 146027 | SC_056 | 1,721,399 | 1,708,261 | 1,678,979 | 1,651,647 | 1,641,513 | 1,641,787 |
| negative sera | | | | | | | |
| Trina #0642 | neg. | 657 | 613 | 638 | 626 | 623 | 610 |
| Trina #0643 | neg. | 698 | 703 | 699 | 704 | 687 | 665 |
| Trina #0644 | neg. | 660 | 653 | 638 | 636 | 620 | 616 |
| Trina #0646 | neg. | 634 | 617 | 634 | 628 | 621 | 613 |
| Trina #0647 | neg. | 623 | 614 | 606 | 620 | 618 | 623 |
| interference sera | | | | | | | |
| C131839 | false positive | 4,206 | 3,707 | 3,364 | 2,996 | 2,309 | 1,383 |
| C132663 | false positive | 11,128 | 1,812 | 1,119 | 895 | 729 | 651 |
| R179865 | elev. signal | 1,630 | 1,338 | 1,219 | 1,114 | 1,000 | 873 |
| R183554 | elev. signal | 1,015 | 894 | 883 | 819 | 790 | 740 |
| C132976 | false positive | 4,866 | 4,041 | 3,454 | 2,911 | 2,057 | 1,230 |

R1 EcSS-TpN17-Bi(DDS)
R2 PmSS-TpN17-BPRu(SK(2)DSS)

TABLE 4

| Oligomeric TpN17; addition of oligomeric VcLp15 | | | | |
|---|---|---|---|---|
| | | EcSkp-VcLp15 | | |
| R1 c (μg/ml) | | 0 counts | 0.1 counts | 1.0 counts |
| positive sera | | | | |
| PLTP_121 | 1:50 | 230,387 | 225,976 | 104,039 |
| PLTP_121 | 1:100 | 116,383 | 112,747 | 55,150 |
| BM 140149 | SC_052 | 1,136,096 | 1,077,292 | 508,996 |
| BM 200680 | SC_054 | 826,355 | 737,483 | 354,883 |
| BM 145855 | SC_055 | 745,762 | 704,713 | 322,241 |
| BM 146027 | SC_056 | 1,446,006 | 1,380,464 | 1,192,282 |
| negative sera | | | | |
| Trina #0642 | neg. | 750 | 757 | 744 |
| Trina #0646 | neg. | 840 | 847 | 815 |
| Trina #0872 | neg. | 846 | 805 | 750 |
| Trina #0873 | neg. | 764 | 763 | 754 |
| interference sera | | | | |
| R179865 | false positive | 3,951 | 1,580 | 782 |
| C131839 | false positive | 6,142 | 4,805 | 1,587 |
| C132663 | false positive | 16,565 | 2,510 | 755 |
| C132723 | false positive | 7,868 | 4,406 | 875 |
| R183554 | false positive | 10,511 | 8,747 | 1,306 |
| C132976 | false positive | 6,274 | 3,062 | 1,088 |

R1 EcFkpA-TpN17-Bi(DDS)
R2 EcSkp-TpN17-BPRu(SK(2)DSS)

TABLE 5

| Monomeric TpN17; addition of oligomeric VcLp15 | | | | |
|---|---|---|---|---|
| | | EcSkp-VcLp15 | | |
| R1 c (μg/ml) | | 0 counts | 0.1 counts | 1.0 counts |
| positive sera | | | | |
| PLTP_121 | 1:50 | 235,946 | 221,210 | 112,238 |
| PLTP_121 | 1:100 | 118,333 | 113,770 | 60,259 |
| BM 140149 | SC_052 | 1,142,874 | 1,048,211 | 637,784 |
| BM 200680 | SC_054 | 757,518 | 672,745 | 382,894 |
| BM 145855 | SC_055 | 861,637 | 823,346 | 475,266 |
| BM 146027 | SC_056 | 1,550,267 | 1,553,275 | 1,516,740 |
| negative sera | | | | |
| Trina #0642 | neg. | 673 | 673 | 632 |
| Trina #0646 | neg. | 651 | 659 | 646 |
| Trina #0872 | neg. | 680 | 683 | 639 |
| Trina #0873 | neg. | 690 | 661 | 651 |
| interference sera | | | | |
| C132221 | elev. signal | 1,301 | 1,204 | 950 |
| C131839 | false positive | 3,928 | 3,108 | 1,144 |
| C132663 | false positive | 11,457 | 2,270 | 671 |
| C132927 | elev. signal | 1,551 | 1,284 | 877 |
| R183554 | elev. signal | 1,003 | 858 | 672 |
| C132976 | false positive | 4,476 | 2,373 | 829 |

R1 EcSS-TpN17-Bi(DDS)
R2 PmSS-TpN17-BPRu(SK(2)DSS)

The invention claimed is:

1. A method for detecting antibodies against the TpN17 antigen of *Treponema pallidum* in an isolated sample comprising contacting the sample with a peptide sequence of *Vibrio cholerae* lipoprotein 15 (VcLp 15) comprising SEQ ID NO:1.

2. A method according to claim 1 wherein a peptide sequence according to UniProt ID Q9KQN6 (SEQ ID NO. 1) or SEQ ID NO. 2 or a partial sequence of SEQ ID NOs. 1 or 2 is used the peptide sequence of *Vibrio Cholera* lipoprotein 15 (VcLpl5) is SEQ ID NO: 1 or SEQ ID NO: 2.

3. A method according to claim 2 wherein said partial sequence of VcLp15 comprises amino acids 26-163 of SEQ ID NOs. 1 or 2.

4. A method according to claim 1 wherein said VcLp15 peptide sequence or partial sequence thereof is fused to a chaperone.

5. A method for detecting antibodies against the TpN17 antigen of *Treponema pallidum* in an isolated sample, said method comprising a) forming an immunoreaction admixture by admixing a body fluid sample with a specific binding partner that can be specifically bound by said antibodies present in said sample;

b) adding SEQ ID NO. 1 or 2 and a chaperone to said immunoreaction admixture either before, at the same time or after said specific binding partner is added to said sample;

c) maintaining said immunoreaction admixture for a time period sufficient for allowing the antibodies present in said body fluid sample to immunoreact with said specific binding partner to form an immunoreaction product; and d) detecting the presence and/or the concentration of any of said immunoreaction product.

6. A method according to claim 5 wherein two TpN17 antigens are used as specific binding partners for the antibodies to be detected in the isolated sample, a first TpN17 antigen that comprises a TpN17 sequence and a first chaperone wherein said first TpN17 antigen can be bound to a solid phase, a second TpN17 antigen that comprises a TpN17 sequence and a second chaperone wherein said second TpN17 antigen carries a detectable label, wherein both TpN17 antigen are identical or immunologically cross-reactive so that they can be bound specifically by the antibodies present in the sample, and wherein the first and the second chaperones are different.

7. A method according to claim 6 wherein the first TpN17 antigen comprises an *E. coli* FkpA as a chaperone and the second TpN17 antigen comprises *E. coli* Skp as a chaperone.

* * * * *